United States Patent
Arai et al.

(10) Patent No.: US 9,968,932 B2
(45) Date of Patent: May 15, 2018

(54) MICROCHANNEL CHIP FOR MICROPARTICLE SEPARATION, MICROPARTICLE SEPARATION METHOD AND SYSTEM FOR MICROPARTICLE SEPARATION USING CHIP

(71) Applicant: NATIONAL UNIVERSITY CORPORATION NAGOYA UNIVERSITY, Aichi (JP)

(72) Inventors: Fumihito Arai, Aichi (JP); Taisuke Masuda, Aichi (JP); Miyako Niimi, Aichi (JP); Haruki Douke, Aichi (JP); Hayao Nakanishi, Aichi (JP); Seiji Ito, Aichi (JP)

(73) Assignee: National University Corporation Nagoya University, Aichi (JP)

( * ) Notice: Subject to any disclaimer, the term of this patent is extended or adjusted under 35 U.S.C. 154(b) by 33 days.

(21) Appl. No.: 14/436,055

(22) PCT Filed: Oct. 15, 2013

(86) PCT No.: PCT/JP2013/077905
§ 371 (c)(1),
(2) Date: Apr. 15, 2015

(87) PCT Pub. No.: WO2014/061631
PCT Pub. Date: Apr. 24, 2014

(65) Prior Publication Data
US 2015/0246353 A1 Sep. 3, 2015

(30) Foreign Application Priority Data
Oct. 15, 2012 (JP) .................................. 2012-227717

(51) Int. Cl.
*B01L 3/00* (2006.01)
*G01N 15/14* (2006.01)
(Continued)

(52) U.S. Cl.
CPC .......... *B01L 3/502753* (2013.01); *G01N 1/04* (2013.01); *G01N 1/28* (2013.01);
(Continued)

(58) Field of Classification Search
CPC ................. B01L 2300/0861; B01L 2300/0816
(Continued)

(56) References Cited

U.S. PATENT DOCUMENTS

| 6,485,690 B1 * | 11/2002 | Pfost | .................... B01J 19/0046 |
| | | | 422/552 |
| 2009/0098541 A1 | 4/2009 | Southern et al. | |
| 2011/0303586 A1 | 12/2011 | Sim et al. | |

FOREIGN PATENT DOCUMENTS

| JP | 2005110529 A | 4/2005 |
| JP | 2007-186456 A | 7/2007 |

(Continued)

OTHER PUBLICATIONS

First Office Action of JP2014-542131, dated Sep. 19, 2017 (with full English Machine Translation).

(Continued)

*Primary Examiner* — Natalia Levkovich
(74) *Attorney, Agent, or Firm* — McDermott Will & Emery LLP

(57) ABSTRACT

Provided is a microchannel chip, for microparticle separation, which can continuously separate microparticles, from a solution in which microparticles of different particle diameter are mixed, without needing to use an antibody or similar, and without causing clogging. Also provided are a microparticle separation method and a system for microparticle separation using the chip. Microparticles can be captured by using the microchannel chip for microparticle separation, the microchannel chip being characterised by being provided with a plurality of main channels and capture portions that are wider than the main channels and at least one of which is provided to each main channel.

25 Claims, 9 Drawing Sheets

(51) Int. Cl.
*G01N 1/04* (2006.01)
*G01N 1/28* (2006.01)
*G01N 35/08* (2006.01)
*G01N 15/10* (2006.01)

(52) U.S. Cl.
CPC ......... *G01N 15/14* (2013.01); *G01N 15/1434* (2013.01); *G01N 35/08* (2013.01); *B01L 2200/0652* (2013.01); *B01L 2200/0668* (2013.01); *B01L 2300/0816* (2013.01); *B01L 2300/0864* (2013.01); *B01L 2400/086* (2013.01); *G01N 2015/1006* (2013.01); *G01N 2015/149* (2013.01)

(58) Field of Classification Search
USPC .................................................. 422/503, 502
See application file for complete search history.

(56) References Cited

FOREIGN PATENT DOCUMENTS

| JP | 2008-116211 A | 5/2008 |
|---|---|---|
| JP | 2008-136475 A | 6/2008 |
| JP | 2008-539711 A | 11/2008 |
| JP | 2011-163830 A | 8/2011 |
| WO | 2010/142954 A1 | 12/2010 |
| WO | 2010/144745 A2 | 12/2010 |
| WO | 2012/037030 A2 | 3/2012 |

OTHER PUBLICATIONS

Allard et al., "Tumor Cells Circulate in Peripheral Blood of All Major Carcionmas but not in Healthy Subjects or Patients With Nonmalignant Diseases," Clinical Cancer Research, vol. 10, Oct. 15, 2014, pp. 6897-6904.

Riethdorf et al., "Detection of Circulating Tumor Cells in Peripheral Blood of Patients with Metastatic Breast Cancer: A Validation Study of the Cell Search System," Clinical Cancer Research, Feb. 1, 2007, 13(3), pp. 920-928.

Tan et al., "Microdevice for the isolation and enumeration of cancer cells from blood," Biomed Microdevices (2009), vol. 11, pp. 883-892.

Mohamed et al., "Isolation of tumor cells using size and deformation," Journal of Chromatography A, 1216(2009), pp. 8289-8295.

International Search Report issued in International Application No. PCT/JP2013/077905 dated Jan. 7, 2014.

International Preliminary Report on Patentability issued in International Application No. PCT/JP2013/077905 dated Jan. 15, 2015, with English translation.

\* cited by examiner

MICROCHANNEL CHIP FOR MICROPARTICLE SEPARATION, MICROPARTICLE SEPARATION METHOD AND SYSTEM FOR MICROPARTICLE SEPARATION USING CHIP

RELATED APPLICATIONS

This application is the U.S. National Phase under 35 U.S.C. § 371 of International Application No. PCT/JP2013/077905, filed on Oct. 15, 2013, which in turn claims the benefit of Japanese Application No. 2012-227717, filed on Oct. 15, 2012, the disclosures of which are incorporated by reference herein.

TECHNICAL FIELD

The present invention relates to a microchannel chip for microparticle separation, a microparticle separation method and system for microparticle separation using the chip, for separating microparticles of different sizes mixed in a liquid; and more particularly relates to a microchannel chip for separating circulating tumor cells (may hereinafter be abbreviated as CTCs), and a CTC separation method and system for CTC separation using the chip, for selectively capturing CTCs in blood.

TECHNICAL BACKGROUND

CTCs are defined as tumor cells that circulate through the peripheral bloodstream of a patient, and have infiltrated the blood vessels from a primary tumor or a metastatic tumor. Detection of CTCs has received attention in recent years as a method of early detection of metastatic malignant tumors because this method is less invasive than radiography and detection of tumor markers in blood serum, allows accurate diagnosis of metastatic malignant tumors, and may be used as an indicator of patient prognosis prediction and treatment effect.

CTCs are very rare cells and it is known that only about one cell is present in $10^8$ to $10^9$ blood cells contained in the blood of a metastatic cancer patient. For this reason, considerable effort is being given to technical development for accurately detecting rare CTCs from peripheral blood. Principal detection methods developed heretofore include immunohistochemical analysis, PCR analysis, and flow cytometry. However, since CTCs are very rare cells as mentioned above, it is not possible to provide a method for detecting such cells directly from blood. Therefore, a CTC concentration procedure is therefore ordinarily essential as a pretreatment, and the CTC abundance ratio must be brought to a level that falls within the range of the detection method.

Among the various techniques developed as CTC concentration methods, the most widely used methods involve concentration of tumor cells in which specific antigens on the surface of the cells have been targeted. Most of the methods use a technique in which magnetic microparticles, which have immobilized monoclonal antibodies against epithelial cell adhesion molecules (EpCAM), are mixed with blood, and tumor cells are thereafter concentrated using a magnet (see, e.g., Non-Patent Document 1). However, it is known that the expression level of EpCAM varies considerably depending on the type of tumor.

Other concentration methods include techniques for concentration using the size of the cell or other modes as a reference. Isolation by size of epithelial tumor cells (ISET) is a method for filtering and sorting epithelial tumor cells that are larger in size than white blood cells. ISET is a simple method in that blood is filtered using a polycarbonate membrane filter having a pore size of 8 µm, and the method is inexpensive and user friendly. The polycarbonate membrane filter used in this case has pores that are formed by heavy ion irradiation and etching by track etching. However, there is a problem in that the pores have a relatively low density, and two or more pores sometimes overlap. Therefore, the capture efficiency for CTC capture is 50 to 60%, and a simple yet efficient concentration method has yet to be developed.

In order to make CTC detection efficient and accurate, techniques for concentration and detection must be carried out in a consistent manner. Multistage handling operations, e.g., cell dyeing, washing, separation, dispensing, and other operations create CTC loss, and it is preferred that these operations be avoided to the extent possible and that analysis be performed in a single process in an integrated detection device. Cellsearch (Veridex™, Warren, Pa.) is the only device that has received FDA approval as a CTC detection device. This device concentrates CTCs using magnetic microparticles with immobilized anti-EpCAM antibodies in whole blood, the tumor cells are immunostained, and the tumor cells are thereafter counted using an automated fluorescence microscope (see, e.g., Non-Patent Document 2). However, when the device is to be used, large-scale equipment is generally required, a trained operator must be available, and it is difficult to perform accurate bedside examinations in a short period of time.

On the other hand, a small microfluidic device for CTC detection is also known. For example, the microfluidic device for CTC detection developed by Toner, et al. is referred to as a CTC-chip and is composed of 78,000 cylindrical structures (micro-posts) in a silicon channel formed by photolithography. Anti-EpCam antibodies are coated on the micro-posts, and when blood is sent to the main channel, CTCs in the blood are captured on the micro-posts. The captured CTCs are subjected to immunofluorescence staining which targets an epithelial cell marker (cytokeratin), and the tumor cells are counted using a fluorescence microscope. This device is a small device that fits in the palm of the hand, and yet has a significant advantage in being capable of providing direct analysis of 5 mL or more of blood. It actually detects CTCs from the blood of a metastatic cancer patient, and is capable of detecting mutations that produce resistant to tyrosine kinase inhibitors from recovered CTCs. Although CTC detection using Cellsearch or a CTC-chip has undergone thoroughgoing experimentation and produced results using metastatic cancer patient blood and other actual samples, these techniques operate on the principle of concentrating CTCs using anti-EpCAM antibodies. There is therefore a problem in that EpCAM-negative or slightly positive tumor cells cannot be detected.

In another method, microfluidic devices for detecting CTCs are being developed using the size and mode of tumor cells as an indicator. In these devices, a membrane micro filter, a crescent-shaped cell-capturing well (see Non-Patent Document 3), or channels having four magnitudes of narrowness (see Non-Patent Document 4) are arranged in the channel structures thereof, and blood cells and tumor cells in the blood are sorted by size to selectively concentrate the tumor cells. The concentrated cells can be dissolved or otherwise manipulated in continuous fashion using the channels. A CTC recovery efficiency of 80% or more is obtained in experiments for evaluating the recovery efficiency of model tumor cells using these devices. However, the evaluation was performed by experimentation using model cells, and no study has been performed in relation to underlying technologies such as cell dyeing and/or washing operations that would be required during actual CTC detection. Furthermore, no experiments have been performed using cancer patient blood or other actual samples, and it is not apparent that these devices could be actually be used for CTC detection.

Furthermore, known small devices that do not use anti-EpCAM antibodies include microfluidic devices provided with a micro-cavity array (very small through-holes) in the microchannels to allow CTCs to be captured (see Patent Document 1). However, the microfluidic devices are of a type that capture CTCs in very small through-holes and therefore have a problem in that work efficiency is reduced due to CTC clogging, and it is furthermore difficult to recover the separated CTC.

PRIOR ARTS LIST

Patent Documents

Patent Document 1: Japanese Laid-open Patent Publication No. 2011-163830

Non-Patent Documents

Non Patent Document 1: Allard W J, Matera J, Miller M C, Repollet M, Connelly M C, Rao C, Tibbe A G, Uhr J W, Terstappen L W. 2004. Tumor cells circulate in the peripheral blood of all major carcinomas but not in healthy subjects or patients with nonmalignant diseases. Clin Cancer Res 10(20):6897-904.

Non Patent Document 2: Riethdorf S, Fritsche H, Muller V, Rau T, Schindlbeck C, Rack B, Janni W, Coith C, Beck K, Janicke F and others. 2007. Detection of circulating tumor cells in peripheral blood of patients with metastatic breast cancer: a validation study of the CellSearch system. Clin Cancer Res 13(3):920-8.

Non Patent Document 3: Tan S J, Yobas L, Lee G Y, Ong C N, Lim C T. 2009. Microdevice for the isolation and enumeration of cancer cells from blood. Biomed Microdevices 11(4):883-92.

Non Patent Document 4: Mohamed H, Murray M, Turner J N, Caggana M. 2009. Isolation of tumor cells using size and deformation. J Chromatogr A 1216(47):8289-95.

SUMMARY OF THE INVENTION

Problems to be Solved by the Invention

The present invention was devised in order to solve the above-described conventional problems, and after thoroughgoing research, a novel finding was made in which microparticles are caused to precipitate in microchannels formed in a chip using a force generated by a meniscus at the air-liquid boundary so that it is possible to capture only objective microparticles in capture portions provided in the microchannels, using (1) a microchannel chip for microparticle separation comprising a plurality of main channels, and one or more capture portions, which have a greater width than that of the main channels, provided to each of the main channels, or (2) a microchannel chip for microparticle separation, comprising: a plurality of main channels; a plurality of branching channels that branch from the main channels and reconnect to the main channels; and a capture portion, which has a greater width than that of the branching channels, provided to the branching channels.

The present invention was perfected after a further novel finding was made in which CTCs alone can be continuously separated out and recovered even using whole blood as a sample when a microchannel chip for microparticle separation, a thin plate for a sample liquid, and a thin plate for a sheath liquid are caused to move in a relative fashion to thereby generate a meniscus, and in which CTCs alone can be continuously separated out and recovered with good operability when a sample is suctioned to generate a meniscus without relative movement of a cover plate and the microchannel chip for microparticle separation.

Specifically, it is an object of the present invention to provide a microchannel chip for microparticle separation, a microparticle separation method and a system for microparticle separation using said chip.

Means to Solve the Problems

As shown below, the present invention relates to a microchannel chip for microparticle separation, a microparticle separation method and system for microparticle separation using said chip.

(1) A microchannel chip for microparticle separation comprising a plurality of main channels, and one or more capture portions, which have a greater width than that of the main channels, provided to each of the main channels.

(2) The microchannel chip for microparticle separation according to (1), wherein the width A of the main channel satisfies $Y<A<X$, the width B of the capture portions satisfies $1X<B<10X$, the depth C in the capture portions satisfies $1X<C<10X$, the depth D of the main channel in the capture portions satisfies $Y<D$, and the depth E of the main channels other than the capture portions satisfies $E=C+D$, where X is the size of microparticles to be captured in the capture portions, and Y is the size of the microparticles to be separated out and removed.

(3) The microchannel chip for microparticle separation according to (2), wherein the width B of the capture portions satisfies $1X<B<2X$, and the depth C of the capture portions satisfies $1X<C<2X$.

(4) The microchannel chip for microparticle separation according to (2) or (3), wherein the width A of the main channel satisfies $Y<A<0.8X$.

(5) A microchannel chip for microparticle separation, comprising: a plurality of main channels; one or more branching channels that branch from the main channels and reconnect to the main channels; and a capture portion, which has a greater width than that of the branching channels, provided to the branching channels.

(6) The microchannel chip for microparticle separation according to claim 5, wherein the width F of the main channels and the branching channels satisfies $Y<F<X$, the width G of the capture portion satisfies $1X<G<10X$, and the depth H of the main channels, the branching channels, and the capture portion satisfies $1X<H<10X$, where X is the size of microparticles to be captured in the capture portion, and Y is the size of the microparticles to be separated out and removed.

(7) The microchannel chip for microparticle separation according to (6), wherein the width G of the capture portion satisfies $1X<G<2X$, and the depth H of the main channels, the branching channels, and the capture portion satisfies $1X<H<2X$.

(8) The microchannel chip for microparticle separation according to (6) or (7), wherein the width F of the main channels and the branching channels satisfies Y<F<0.8X.
(9) The microchannel chip for microparticle separation according to any one of (6) to (8), wherein a channel having a width F and a depth J, where Y<J, is furthermore provided below the main channels, the branching channels, and the capture portion.
(10) The microchannel chip for microparticle separation according to any one of (1) to (9), comprising a drainage channel linked to one end of the plurality of main channels.
(11) The microchannel chip for microparticle separation according to any one of (1) to (10), wherein the microparticles to be captured in the capture portion are CTCs and the microparticles to be removed are blood cells.
(12) A system for microparticle separation comprising: the microchannel chip for microparticle separation according to any one of (1) to (11); a thin plate for sample liquid; a thin plate for sheath liquid; and suction means and/or a suction device for suctioning sheath liquid.
(13) A system for microparticle separation comprising: the microchannel chip for microparticle separation according to any one of (1) to (11); a cover plate; and suction means and/or a suction device.
(14) The system for microparticle separation according to (12) or (13), furthermore comprising a suction unit having a lateral groove and a suction hole in communication with the lateral groove.
(15) The system for microparticle separation according to any one of (12) to (14), wherein a magnetic field generator and/or an electric field generator is provided in a capture portion of the microchannel chip for microparticle separation.
(16) A microparticle separation method comprising: injecting a sample liquid between a thin plate for a sample liquid and the microchannel chip for microparticle separation according to any one of (1) to (11); injecting a sheath liquid between a thin plate for a sheath liquid and the microchannel chip for microparticle separation; and causing the microchannel chip for microparticle separation, the thin plate for a sample liquid and the thin plate for a sheath liquid to move in a relative fashion to generate a meniscus, whereby objective microparticles are captured in capture portions provided to the microchannel chip for microparticle separation, and microparticles to be removed are removed from the microchannel chip for microparticle separation by the sheath liquid suctioned by suction means and/or a suction device.
(17) A microparticle separation method comprising: injecting a sample liquid between a cover plate and the microchannel chip for microparticle separation according to any one of (1) to (11); and capturing objective microparticles in capture portions provided to the microchannel chip for microparticle separation by a meniscus generated as a result of the sample liquid being suctioned by suction means and/or a suction device.
(18) The microparticle separation method according to (17), comprising: injecting a sheath liquid between the cover plate and the microchannel chip for microparticle separation after the sample liquid has been suctioned; and suctioning the sheath liquid with the aid of suction means and/or a suction device to thereby wash away remaining microparticles to be removed.

Advantageous Effects of the Invention

The system for microparticle separation of the present invention is capable of separating, with high precision in a short period of time, only CTCs without pretreatment from whole blood containing microparticles, e.g., red blood cells, white blood cells, and the like, of different sizes in a liquid. Therefore, bedside cancer diagnosis is possible using a simple operation.

The microchannel chip for microparticle separation used in the system for microparticle separation of the present invention does not use anti-EpCAM antibodies, and therefore even CTC-negative or slightly positive tumor cells can be reliably detected. The microchannel chip for microparticle separation of the present invention allows red blood cells, white blood cells, and other small-sized cells to flow to the exterior of the chip by way of the sheath liquid, is capable of capturing CTCs and other large-sized cells in capture portions provided to the channels, and is therefore capable of continuous processing without device clogging, which is different from conventional filter-type devices.

The microchannel chip for microparticle separation used in the system for microparticle separation of the present invention is capable of being mass produced using semiconductor formation processes, and the cost of a CTC examination can therefore be considerably reduced.

CTCs alone can be continuously separated out and recovered even using whole blood when the microchannel chip for microparticle separation, a thin plate for a sample liquid, and a thin plate for a sheath liquid are caused to move in relative fashion to generate a meniscus.

On the other hand, the operability of a system for microparticle separation can be improved because there is no need for a relative movement operation with a gap maintained between the microchannel chip for microparticle separation and a cover plate when a sample is suctioned to generate a meniscus without relative movement of the cover plate and the microchannel chip for microparticle separation. When the cover plate is formed with a size that covers all the main channels formed in the microchannel chip for microparticle separation, a meniscus can be generated in many main channels at one time in contrast with using relative movement, and processing efficiency can therefore be improved.

DESCRIPTION OF THE EMBODIMENTS

The microchannel chip for microparticle separation, and the microparticle separation method and system for microparticle separation using the chip are described in detail below.

Figure 1:
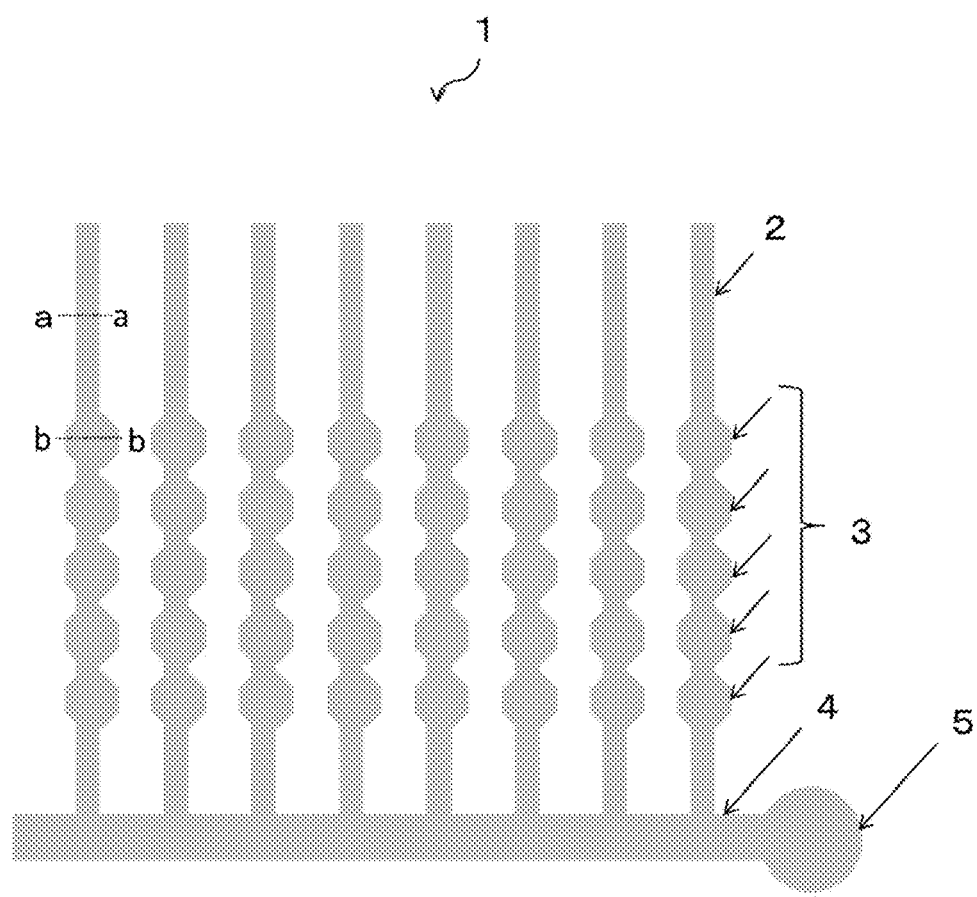
FIG. 1 is schematic view showing an example of the microchannel chip for microparticle separation of the present invention.

FIG. 1 shows an example of the microchannel chip for microparticle separation of the present invention, the microchannel chip 1 for microparticle separation having main channels 2, a plurality of capture portions 3 provided to the main channels 2, a drainage channel 4 linked to one end of the plurality of main channels 2, and a drainage port 5 for fluid to be drained from the drainage channel 4. In the present invention, the term "microparticles" refers to particles that can be dispersed in a liquid, and the particle mode may a separated or aggregated state. The size of the microparticles is not particularly limited as long as the range allows the principles of a meniscus to be applied. The size can be about 1 mm or less. Also, the phrase "a plurality of main channels" means at least two or more main channels.

Figure 2:
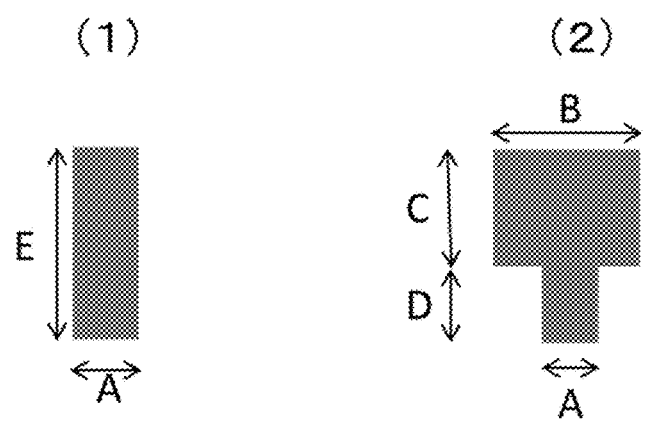
FIG. 2 is view showing the cross section of the main channel 2 of FIG. 1.

FIG. 2 is view showing the cross section of the main channel 2 of FIG. 1, where (1) is cross-sectional view of the position a-a in which a capture portion 3 of the main channels 2 is not provided, and (2) is a cross-sectional view of the position b-b in which a capture portion 3 of the main channels 2 is provided. The width and depth of the main channels 2 and the width and depth of the capture portions 3 can be set, as appropriate, in accordance with the size of the objective to be separated out, but since the microparticles to be removed in the channel in the lower portion of FIG. 2(2) are drained from the chip using a later-described sheath liquid and the objective microparticles are captured in the capture portions in the upper portion, it is preferred that the width A of the main channels 2 satisfy $Y<A<X$, the width B of the capture portions 3 satisfy $1X<B<10X$, the depth C in the capture portions 3 satisfy $1X<C<10X$, the depth D of the main channel in the capture portions 3 satisfy $Y<D$, and the depth E of the main channels other than the capture portions 3 satisfy $E=C+D$, where X is the size of microparticles to be captured in the capture portions, and Y is the size of the microparticles to be separated out and removed. When B and C are 10X or more, the width of the main channels 2 with respect to the size of the plurality of capture portions 3 is excessively small, and this is not preferred in that the processing capability for separating out and removing microparticles is reduced. The inequalities $1X<B<10X$ and $1X<C<10X$ are examples of the main channels 2 in the lower portion of the capture portions 3 being integrated, but B and C may be 10X or greater if a plurality of main channels 2 is provided to the lower portion of the capture portions 3 to increase the processing capability for separating out microparticles.

Also, the numerical values are in the range for the case of concentrating objective particles or otherwise capturing a plurality of microparticles in a capture portion, but the range can be $1X<B<2X$ and $1X<C<2X$ in the case that a single microparticle is to be captured in each of the capture portions 3 for subjecting the captured microparticles to analysis or other procedure. Furthermore, when the objective microparticles captured in the capture portions 3 are biological cells or other microparticles whose shape readily changes, it is possible that the cell will deform under fluid force and slip out from the capture portions 3. Accordingly, the width A of the main channels can be selected, as appropriate, in accordance with the change ratio of the shape of the objective microparticles, and in the case of CTCs, the width A of the main channels 2 may be set to, e.g., $Y<A<0.8X$.

When CTCs are to be captured and red blood cells, white blood cells, and other blood cells other than CTCs are to be removed from whole blood, the width A of the main channels 2 can be less than the diameter (15 to 30 μm) of the CTCs and greater than the diameter (about 7 μm) of red blood cells, white blood cells, and other blood cells, preferably 8 to 12 μm. On the other hand, the shape of the capture portions 3 is not particularly limited as long as CTCs can be captured, and examples include circular, substantially square, hexagonal, octagonal, and other polygonal shapes. Since CTCs must be captured in the capture portions 3, the width B and depth C of the capture portions 3 must be a size greater than the diameter of the CTC, preferably 16 to 36 μm. The width of the capture portions 3 refers to the diameter when the shape of the capture portions 3 is circular, when the shape is square, the width refers to one side, and when the shape is hexagonal, octagonal, or other polygonal shape, the width refers to the shortest length that passes through the center of the polygonal shape.

In the capture portions 3, CTCs are captured in the upper portion shown in (2) and blood cells are removed in the later-described sheath liquid in the main channels 2 of the lower portion. Therefore, the depth D of the main channels 2 must be greater than at least the diameter of blood cells. Also, it is preferred that one or more blood cells be removed simultaneously, and the depth D is therefore preferably 8 to 20 μm. The depth E of the main channels 2 in which capture portions 3 are not provided can be C+D.

The size in the above-described example is for the case of separating CTCs from whole blood, but when blood cells or mesothelial cells (about 7 to 15 μm) are to be separated out from an aggregation of stomach cancer cells (25 to 50 μm) in, e.g., an abdominal cleaning solution, the depth D of the main channels 2 can be 8 to 24 μm, can the width B and depth C of the capture portions 3 can be 26 μm to 60 μm.

Figure 3:
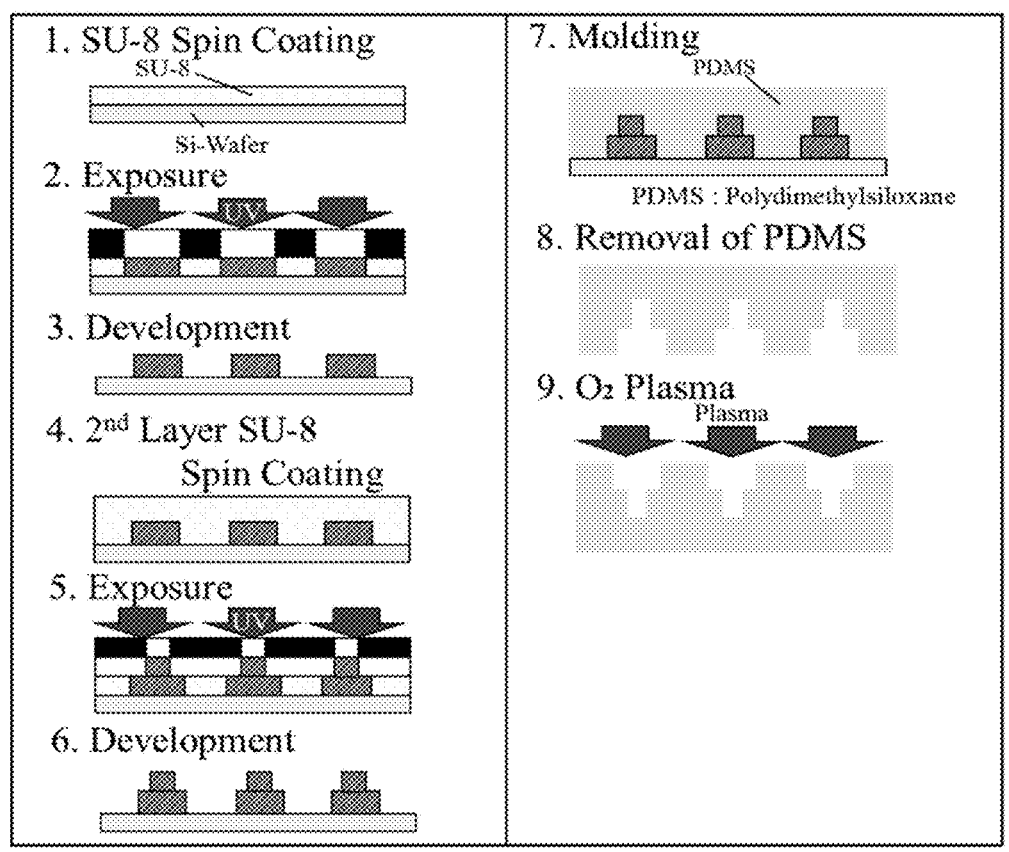
FIG. 3 is a flowchart showing the procedure for fabricating the microchannel chip for microparticle separation.

The microchannel chip for microparticle separation can be fabricated using photolithographic techniques. FIG. 3 is a flowchart showing an example of fabrication procedure, and since the microchannel chip for microparticle separation shown in FIGS. 1 and 2 is a two-stage shape, fabrication can be carried out using two-stage exposure techniques.

First, a silicon substrate is organically washed by an ultrasonic washer, and then baked. Fabrication is subsequently carried out in accordance with the following procedure shown in FIG. 3.

1. A negative photoresist (SU-8) spin-coated on a Si substrate and then prebaked on a hot plate.
2. The substrate is exposed using a chrome mask or other photomask.
3. The substrate is subjected to post-exposure baking on a hot plate, developed using development solution (PM thinner or the like), and thereafter rinsed using ultrapure water. Moisture is dispersed using a spin drier or the like to dry.
4. A second SU-8 negative photoresist is spin-coated and the substrate is prebaked.
5. The substrate is exposed using a chrome mask or other photomask.
6. The substrate is subjected post-exposure baking, and then developed, rinsed, and has a pattern formed thereon.
7. The formed pattern is transferred to polydimethylsiloxane (PDMS).
8. The PDMS is separated from the formed pattern.
9. The PDMS surface is hydrophilized.

The organic washing is not particularly limited, and may be performed using acetone, ethanol, or other washing agent generally used in the field of semiconductor manufacturing. In the above-described procedure, an example is described using Si as the substrate, but the substrate material is not particularly limited as long as the material is generally used in the technical field of photolithography. Examples include silicon carbide, sapphire, gallium phosphide, gallium arsenide, gallium phosphide, and gallium nitride. The negative photoresist is also not limited to SU-8. It is also possible to use, e.g., KMPR or the like, and if a positive photoresist is to be used, examples would include PMER, AZ, or another generally used resist.

Although PDMS was used in the above-described procedure, examples of the material of the microchannel chip for microparticle separation of the present invention also include poly(methyl methacrylate) (PMMA), PC, hard polyethylene plastic, hydrogel, and glass.

Hydrophilizing the chip surface makes it possible to prevent air bubbles from entering the grooves when liquid is injected into the microchip. Examples of the hydrophilizing treatment include plasma treatment, surfactant treatment, PVP (polyvinyl pyrrolidone) treatment, and photocatalytic treatment. For example, subjecting the chip surface to a plasma treatment for 10 to 30 seconds makes it possible to introduce a hydroxyl group to the chip surface. The treatment for hydrophilicity the chip surface may be used to make hydrophilic solely the main channels, later-described branching channels, and capture portions. Since the portions other than the main channels, the branching channels, and capture portions would not be hydrophilized, the sample liquid and/or sheath liquid can more readily flow to the main channels, the branching channels and the capture portions, and the efficiency of capturing microparticles can be improved. The treatment for hydrophilizing the main channels, the branching channels, and the capture portions can be carried out by covering the other portions with a mask or the like and using the same method as described above. Alternatively, the mask may be positive-negative inverted and a fluororesin or the like may be vapor-deposited to perform a hydrophobic treatment.

Figure 4:
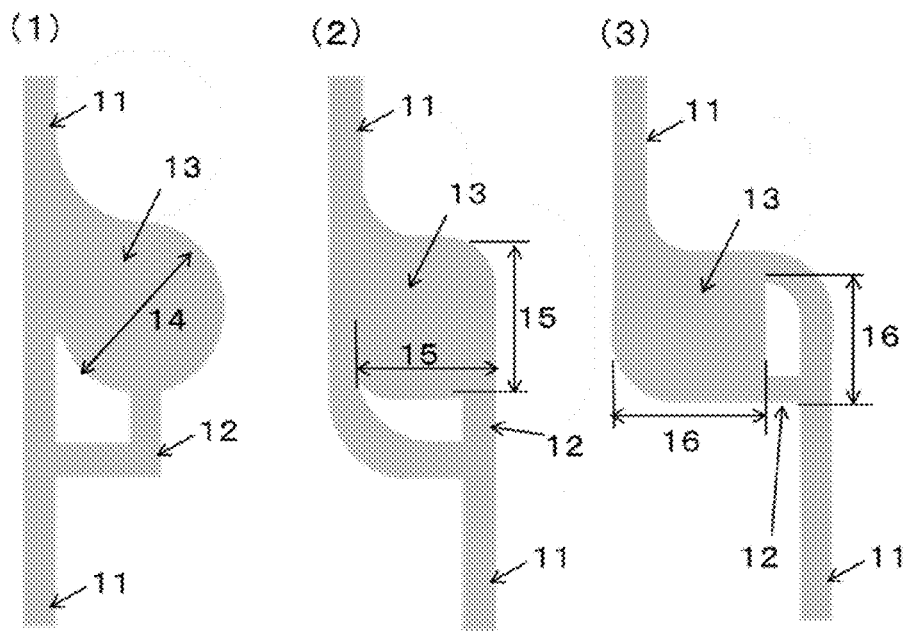
FIG. 4 is a view showing an outline of another example of the microchannel chip for microparticle separation of the present invention.

FIG. 4 is a view showing an outline of another example of the microchannel chip for microparticle separation of the present invention. In the examples shown in (1) to (3) of FIG. 4, a branching channel 12 that branches from a main channel 11 is provided, a capture portion 13 is provided in the branching channel 12, and the branching channel 12 reconnects to the main channel 11. The capture portion 13 provided to the branching channel 12 may be in contact with the main channel 11, as shown in (1) to (3) of FIG. 4. (1) shows an example in which the capture portion 13 provided to the branching channel is circular in shape; (2) shows an example in which a capture portion 13 substantially square in shape with smooth corners is provided in a direction perpendicular to the flow direction of the main channel 11; and (3) shows an example in which a capture portion 13 substantially square in shape with smooth corners is provided in the flow direction of the main channel 11 and the flow direction of the main channel 11 has been changed about 90 degrees.

The width and depth of the main channel 11 and the branching channel 12, and the size of the capture portion 13 can be set, as appropriate, in accordance with the size of the objective to be separated out. However, the width F of the main channel 11 and the branching channel 12 preferably satisfies $Y<F<X$, where X is the size of microparticles to be captured in the capture portions 13, and Y is the size of the microparticles to be separated out and removed, in the same manner as the microchannel chip for microparticle separation shown in FIG. 2. The width G of the capture portion 13 preferably satisfies $1X<G<10X$, and the depth H of the main channel 11, the branching channel 12, and the capture portion 13 preferably satisfies $1X<H<10X$; and when a plurality of branching channels 12 linking to the capture portion 13 is to be provided, G and H may be 10X or greater. When a single microparticle is to be captured in the capture portion 13, it is preferred that $1X<G<2X$ and $1X<H<2X$. Furthermore, when the objective microparticle to be captured in the capture portion 13 is a biological cell or other objective whose shape readily changes, it is preferred that $Y<F<0.8X$. When channels are to be further provided below the capture portion 13, channels in which the width is F and the depth J is $Y<J$ are preferably provided below the main channel 11, the branching channel 12, and the capture portion 13.

For example, when CTCs are to be captured from whole blood and red blood cells, white blood cells, and other cells other than CTCs are to be removed, the width of the main channel 11 can be less than the diameter of the CTCs (15 to 30 μm) and greater than the diameter of blood cells (about 7 μm), preferably 8 to 12 μm. On the other hand, the capture portion 13 must capture CTCs and the size of the capture portion 13 must be greater than the diameter of the CTC. For example, when the capture portion 13 of FIG. 4(1) is circular, the diameter 14 is preferably 16 to 36 μm, and when the capture portion 13 of (2) and (3) is substantially square, the sides 15, 16 are preferably 16 to 36 μm. The shape of the capture portion 13 is not particularly limited as long as the shape is capable of capturing CTC, and may be hexagonal, octagonal, or other polygonal shape. In the case of a polygonal shape, the length of the shortest line that passes though the center can be 16 to 36 μm as above.

In the case of a microchannel chip for microparticle separation having the shapes shown in FIGS. 4(1) to (3), the CTCs are trapped by the capture portion 13, a later-described sheath liquid flows through the main channel 11, and the CTCs do not therefore undergo the fluid force of the sheath liquid. Furthermore, many of the blood cells other than CTCs flow through the main channel 11 together with the later-described sheath liquid, and the blood cells that have flowed into the capture portion 13 pass through the branching channel 12 extending from the capture portion 13 and are able to again return to the main channel 11. Therefore, in contrast to the microchannel chip for microparticle separation shown in FIGS. 1 and 2, the main flow of CTCs and cells other than CTCs is different in the microchannel chip for microparticle separation shown in FIG. 4, and therefore, it is not essential that a channel be formed below the capture portion 13. When a channel is not provided therebelow, the depth of the main channel 11, the branching channel 12, and the capture portion is preferably 16 to 36 μm. When a channel is provided below the capture portion 13, the depth of the channel below the capture portion 13 is preferably 8 to 20 μm in the same manner as shown in FIG. 2, but the portions other than the capture portion 13 can be set to a depth that is the total of the depth of the capture portion 13 and the channel.

When step is not to be provided, the microchannel chip for microparticle separation having a shape shown in FIG. 4 can be fabricated in using the same procedure as described above using a mask having the shape shown in FIG. 4 except that the procedure for providing a second-stage resist layer of "4 to 6" in the above-described procedure is omitted. When a step is to be provided, the microchannel chip for microparticle separation can be fabricated using the same procedure as described above except that a mask having a shape shown in FIG. 4 is used.

Next, the system for microparticle separation using the microchannel chip for microparticle separation described above and the usage method are next described.

Figure 5:
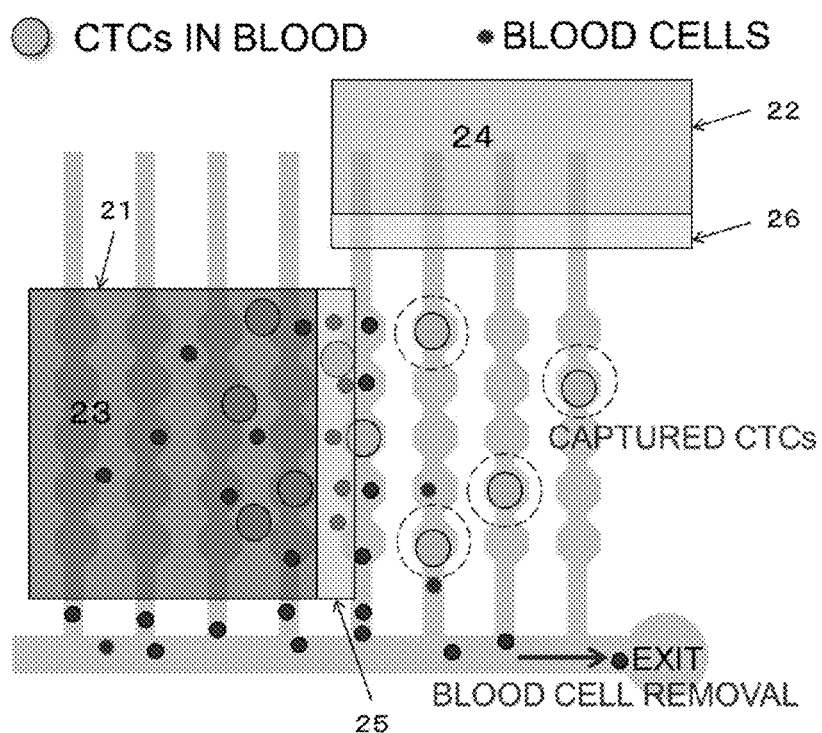
FIG. 5 is a view showing an outline and mode of use of the system for microparticle separation of the present invention, and an embodiment for causing the microchannel chip for microparticle separation and the thin plate for a sample liquid and thin plate for a sheath liquid to move in relative fashion to thereby generate a meniscus.

FIG. 5 is a view showing an outline and mode of use of the system for microparticle separation of the present invention, and shows embodiment for causing the microchannel chip for microparticle separation and the thin plate for a sample liquid and thin plate for a sheath liquid to move in relative fashion to thereby generate a meniscus. The system for microparticle separation of the present embodiment includes a microchannel chip for microparticle separation, a thin plate 21 for a sample liquid, a thin plate 22 for a sheath liquid, and a suction device (not shown) for suctioning a sheath liquid.

The thin plate 21 for a sample liquid and the thin plate 22 for a sheath liquid may be glass, plastic, or the like and are not particularly limited as long as these do not react with the sample and/or sheath liquid. The sheath liquid is not particularly limited as long as the microparticles to be separated out are not damaged or otherwise compromised. When whole blood is used as a sample, the sheath liquid may be a phosphate-buffered saline (PBS), a Tris buffer or various other buffer solutions, a simulated body fluid (SBF), a general cell culture medium, or other generally used sheath liquids may be used, though no particular limitation is imposed thereby.

FIG. 5 shows an example in which whole blood is used as the sample. Whole blood 23 is injected between the microchannel chip 1 for microparticle separation and the thin plate 21 for a sample liquid and the microchannel chip for microparticle separation and the thin plate 21 for a sample liquid are moved in relative fashion to thereby generate a meniscus 25.

Figure 6:
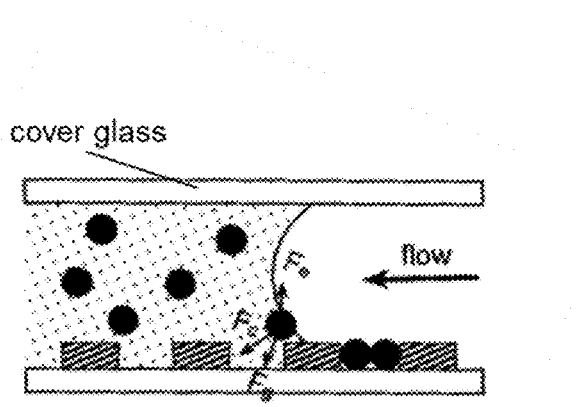
FIG. 6 is a view illustrating the principle for generating a meniscus.

FIG. 6 is a view illustrating the principle for generating a meniscus. In the present invention, a technique is used in which the microparticles are arrayed in a closely packed structure with each other using capillary force (lateral capillary force in particular) between microparticles present in the air-liquid boundary, which is referred to as the advection-aggregation method. When a meniscus composed of a suspension liquid in which microparticles are dispersed in a solution is formed on a substrate, portions in which microparticles partially emerge from the solution are formed at the leading edge of the meniscus as shown in the drawing. In portions of partial emergence, a downward-pressing force produced by gravity and boundary tension is imparted to the microparticles as they move together with the meniscus, and the microparticles are captured in the microchannels provided to the chip. Also, the sheath liquid is also generated a meniscus in the same manner, whereby the sheath liquid readily enters into the main microchannels.

Here, microchannels are formed in a two-step shape as shown in FIG. 2(2), which is a cross-sectional view along the line b-b of FIG. 1, the CTCs are trapped in the upper stage capture portions 3, and blood cells which are small in size fall into the lower-stage channel. Furthermore, a sheath liquid 24 is injected between the microchannel chip 1 for microparticle separation and the thin plate 22 for a sheath liquid on the upstream side of the channels, suction is applied by a suction device (not shown) from the downstream side while the microchannel chip 1 for microparticle separation and the thin plate 22 for a sheath liquid are moved in a relative fashion, whereby the sheath liquid flows from upstream to downstream, and blood cells are washed away while CTCs remain trapped in the capture portions 3, whereby CTCs are efficiently separated out. When a microchannel chip for microparticle separation having a shape shown in FIG. 4 is used, the CTCs are trapped in the capture portions 13, and the other blood cells and the like can be washed away through the main channel 11 and/or the branching channel 12 together with the sheath liquid. In order to generate a meniscus, it is possible immobilize the microchannel chip for microparticle separation and move the thin plate 21 for a sample liquid and thin plate 22 for a sheath liquid, or the thin plate 21 for a sample liquid and the thin plate 22 for a sheath liquid may be immobilized and the microchannel chip for microparticle separation moved.

The gap between the microchannel chip for microparticle separation, and the thin plate 21 for a sample liquid and thin plate 22 for a sheath liquid is preferably 700 to 1000 μm. When the gap is less than 700 μm, the amount of sample liquid to be introduced is reduced and the processing capability is reduced, and when the gap is greater than 1000 μm, the meniscus force is reduced and adequate separation cannot be obtained. The gap can be adjusted using a microstage. The relative movement speed between the microchannel chip for microparticle separation, and the thin plate 21 for a sample liquid and thin plate 22 for a sheath liquid is preferably 20 to 50 μm/s. When the speed is less than 20 μm/s, the processing time is lengthened and processing capability is reduced; and when the speed is greater than 50 μm/s, microparticles are not captured and separation efficiency is reduced.

The flow rate of the sheath liquid is preferably 20 to 500 μm/s. When the flow rate is less 20 μm/s, the separation efficiency is reduced due to a reduced ability to wash away blood cells, and when the flow rate is greater than 500 μm/s, any temporarily captured CTCs are suctioned away and separation efficiency is reduced. The flow rate of the sheath liquid can be adjusted using the suction force of the suction device. The suction device can be a suction pump, a microsyringe, or the like, and is not particularly limited as long as a liquid can be suctioned. The example shown in FIG. 5 is a scheme in which the sheath liquid 24 is injected as required between the microchannel chip for microparticle separation and the thin plate 22 for a sheath liquid, but it is also possible to connect the sheath liquid container or a tube or the like extending from the sheath liquid container to one end of the thin plate 22 for a sheath liquid to thereby allow sheath liquid to be automatically fed.

Figure 7:
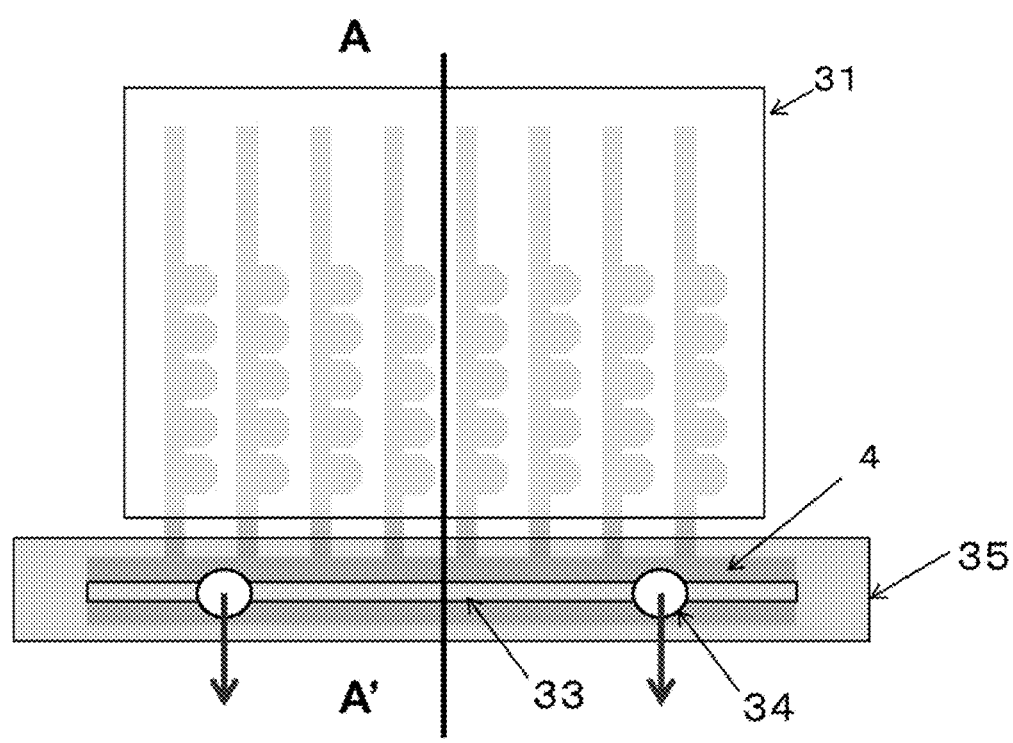
FIG. 7 is a view showing an outline and mode of use of the system for microparticle separation of the present invention, and an embodiment for suctioning a sample without causing the microchannel chip for microparticle separation and the cover plate to move in relative fashion to thereby generate a meniscus.

FIG. 7 is a view showing an outline and mode of use of the system for microparticle separation of the present invention, and an embodiment for suctioning a sample liquid without causing the microchannel chip for microparticle separation and the cover plate to move in relative fashion to thereby generate a meniscus. The system for microparticle separation of the present embodiment comprises at least: a microchannel chip 1 for microparticle separation; a cover plate 31 overlaid on the microchannel chip 1 for microparticle separation, whereby a meniscus is generated by a sample liquid and sheath liquid being suctioned; and suction means and/or a suction device (not shown). In the embodiment shown in FIG. 7, a drainage port 5 is not required to be provided to the microchannel chip 1 for microparticle separation, and the sample liquid and sheath liquid can be suctioned from the drainage channel 4 connected to one end of the plurality of main channels 2. The sample liquid and the sheath liquid may be directly suctioned/drained from the drainage channel 4 using later-described suction means and/or a suction device, or may be suctioned by suction means and/or a suction device via a suction unit 35 comprising a lateral groove 33 formed in the lengthwise direction and a suction hole 34 in communication with the lateral groove 33. In the present embodiment, the later-described suction means and/or suction device may be in close contact with the microchannel chip for microparticle separation to be capable of suctioning the sample liquid and the sheath liquid directly from the main channels 2, and in such a case, a drainage channel 4 is not required. The mode for directly suctioning/draining the sample liquid and the sheath liquid 32 via the suction unit 35 as required using the suction means and/or suction device of the present embodiment can also be applied to the embodiment shown in FIG. 5. In the present embodiment, the sample liquid is suctioned using suction means and/or a suction device to thereby separate out the microparticles contained in the sample liquid, and it is not therefore essential that the sheath liquid flow after the sample liquid has flowed because the sample liquid itself serves as a sheath liquid if a diluted sample liquid is used. When the objective microparticles are to be separated with high purity, it is possible to select whether to use a sheath liquid in accordance with the object of separation, such as washing away remaining microparticles to be removed by allowing a sheath liquid to flow.

Figure 8:
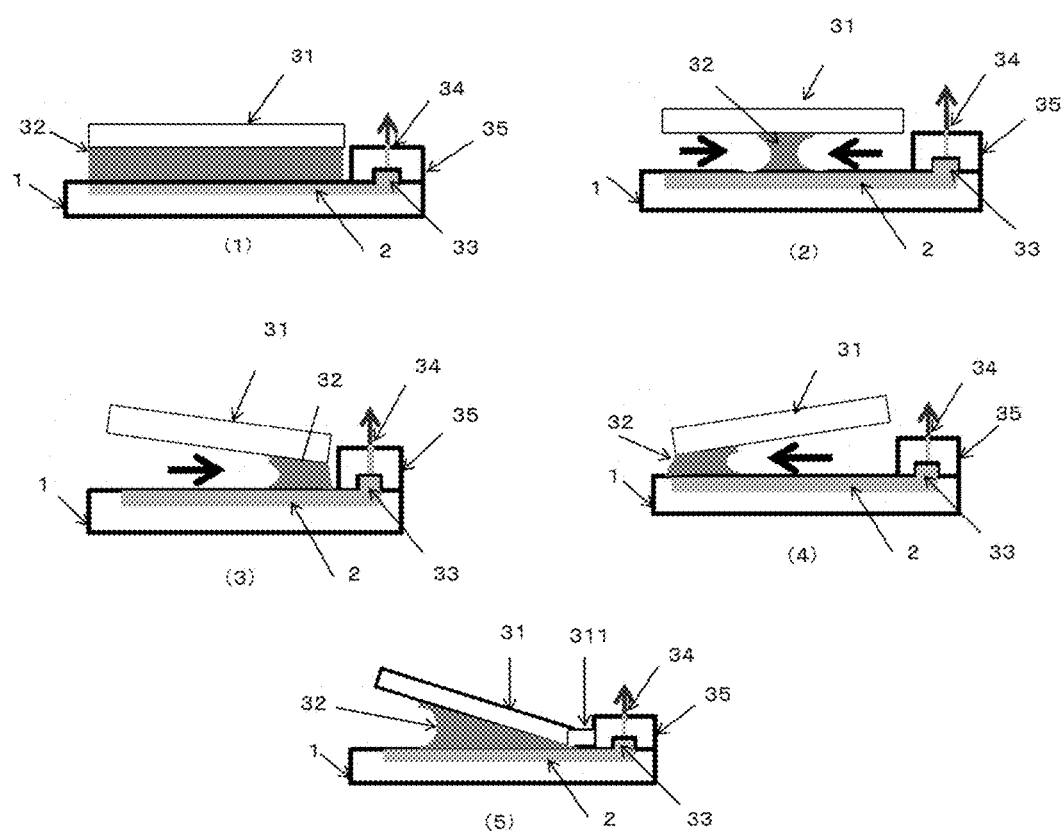
FIGS. 8(1) to 8(5) are a cross-sectional views along the line A-A' of FIG. 7, and are views illustrating the principle for generating a meniscus in the present embodiment.

FIG. 8 is a cross-sectional view along the line A-A' of FIG. 7, and is a view illustrating the principle for generating a meniscus in the present embodiment. When a sample liquid and a sheath liquid 32 are injected between the microchannel chip 1 for microparticle separation and the cover plate 31 and suctioned by suction means and/or a suction device (not shown), as shown in FIG. 8(1), the sample liquid and the sheath liquid 32 are drained from the main channels 2 by way of the drainage channel 4. In this process, a capillary force is generated in the sample liquid and the sheath liquid 32 between the microchannel chip 1 for microparticle separation and the cover plate 31, and a meniscus is therefore generated in the manner shown in FIG. 8(2).

The movement direction of the sample liquid and the sheath liquid 32 shown in FIG. 8(2) is shown for the case in which the cover plate 31 is arranged parallel to the microchannel chip 1 for microparticle separation, and, for example, when the cover plate 31 on the drainage channel 4 side is arranged with a slope so as to be closer to the microchannel chip 1 for microparticle separation, as shown in FIG. 8(3), the sample liquid and the sheath liquid 32 move toward the drainage channel 4 sides due to the pressure applied to the sample liquid and the sheath liquid 32. Conversely, the sample liquid and the sheath liquid 32 move to the opposite side from the drainage channel 4 due to the pressure applied to the sample liquid and the sheath liquid 32 when the cover plate 31 is arranged with a slope so as to be closer to the microchannel chip 1 for microparticle separation on the opposite side of the drainage channel 4 side of the microchannel chip 1 for microparticle separation, as shown in FIG. 8(4). The present invention can be implemented in any of the embodiments of FIGS. 8(2) to (4), but the embodiment shown in FIG. 8(3) is preferred in that the sample liquid and the sheath liquid 32 are closer to the drainage channel 4 side and the suction force of the suction means and/or a suction device can therefore be reduced. The gap between the microchannel chip 1 for microparticle separation and the cover plate 31 is preferably 700 to 1000 μm in the same manner as the thin plate 21 for a sample liquid described above, and adjustment can be made within the range of this gap using a microstage. In the case that the cover plate 31 is sloped, the degree of slope is preferably about 6° to 18°. When the slope angle is less than 6°, the pressure applied to the sample liquid and the sheath liquid is insufficient; and a slope angle greater than 18° is to too great to obtain a meniscus angle that would be effective for capturing microparticles, which is not preferred. The embodiment shown in FIG. 8(5) has a second cover plate 311 so that the meniscus of the sample liquid and the sheath liquid 32 is not generated on the suction side, and since a closed channel system can be configured, it is possible to provide stable suctioning.

The cover plate 31 and the second cover plate 311 can be fabricated using the same material as the thin plate 21 for a sample liquid described above. The size of the cover plate 31 is not particularly limited, but in the present embodiment, a meniscus can be generated without moving the cover plate 31. Therefore, in order to improve processing efficiency, it is desirable for the cover plate to be formed to a size that allows all the main channels 2 formed in the microchannel chip 1 for microparticle separation to be covered. In relation to the size of the second cover plate 311, the length in the lateral direction orthogonal to the main channels 2 can be the same length as the cover plate 31 and the width can be adjusted, as appropriate, in a range in which a meniscus is not generated.

Examples of means for suctioning the sample liquid and the sheath liquid 32 include a fabric, cotton, sponge, chamois, or other suctioning pad, and the suction pad can be placed in direct contact with the drainage channel 4 or the main channels 2 to suction/drain the adjacent lane and sheath liquid.

Figure 9:
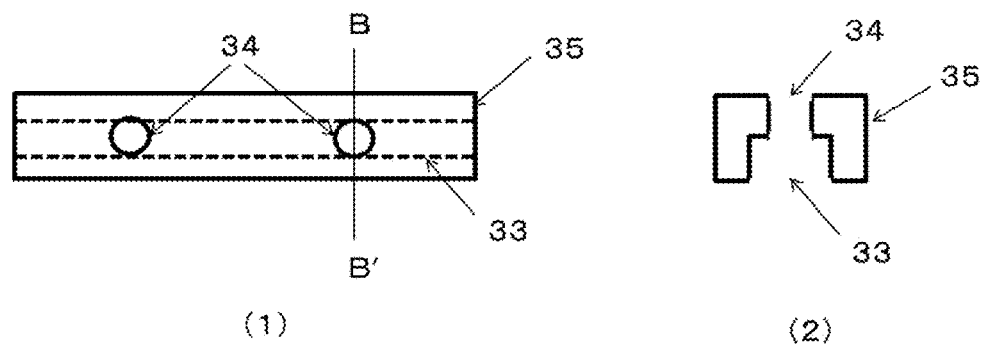
FIG. 9(1) is a top view showing an outline of the suction unit 35, and FIG. 9(2) shows a cross section along the line B-B' of the suction unit 35.

Suctioning/draining the sample liquid and the sheath liquid 32 may be carried out via the suction unit 35. FIG. 9(1) is a top view showing an outline of the suction unit 35, and FIG. 9(2) shows a cross section along the line B-B' of the suction unit 35. The suction unit 35 is provided with a lateral groove 33 capable of suctioning the sample liquid and the sheath liquid 32 using capillary force, and a suction hole in communication with the lateral groove 33 and for connecting to a suction device (not shown). Since at least the removed microparticles must be allowed to pass, the width of the lateral groove 33 is preferably at least 8 μm or more when the sample is whole blood, and more preferably 10 μm or more in order to increase processing capability. On the other hand, the width of the lateral groove 33 does not have a particular upper limit as long as capillary force is generated, and the upper limit can be adjusted, as appropriate, with consideration given to the amount of sample liquid and sheath liquid to be suctioned, the capillary force, and the like. For example, a width of about 200 µm can be provided. Bringing the suction unit 35 into contact with the drainage channel 4 or atop the main channels 2 and suctioning the sample liquid and the sheath liquid 32 into the lateral groove 33 using capillary force makes it possible for the sample liquid and the sheath liquid 32 to be drained from the drainage channel 4 or the main channels 2. The sample liquid and the sheath liquid 32 suctioned into the lateral groove 33 can be suctioned/drained through the suction hole 34 using a pump, micro-syringe, or other suction device. When the amount of sample liquid and sheath liquid to be drained is considerable and cannot be suctioned out using only the lateral groove 33, it is also possible to use a suction device in combination with the lateral groove. The number of suction holes 34 is not particularly limited, and it is possible to provide a number sufficient to ensure no considerable difference in the flow rate of the sample liquid and sheath liquid 32 that flow through the main channels 2.

The width of the lateral groove 33 may be increased and the above-noted fabric, cotton, sponge, chamois, or other suction means inserted into the lateral groove 33, and the sample liquid and the sheath liquid 32 absorbed into the suction means can be suctioned by a suction device through the suction hole 34. In the present embodiment, the flow rate of the sample liquid and the sheath liquid flowing through the main channels 2 is adjusted by the suction force of the suction means and/or a suction device. Accordingly, the speed at which the sample liquid and the sheath liquid are suctioned can be more stably maintained by furthermore suctioning the sample liquid and sheath liquid suctioned to the suction means by a suction device in comparison with merely suctioning the sample liquid and the sheath liquid 32 by suction means or suctioning the sample liquid and the sheath liquid 32 into the lateral groove 33 by capillary force. The suction device and suction hole 34 can be connected using a tube composed of silicone or the like.

The material constituting the suction unit 35 is not particularly limited and may be acrylic, nylon, Teflon (registered trademark), or other resin, or glass or the like, as long as it does not react with the sample liquid or the sheath liquid. The suction unit 35 can be fabricated by cutting using a drill, end mill, or other cutting tool, or by fabricating a mold in the shape of the suction unit 35 and using injection molding.

The system for microparticle separation of the present embodiment is capable of trapping CTCs in, e.g., a blood sample in the capture portions and washing away the other blood cells and the like together with the sheath liquid by first inserting a sample liquid between the microchannel chip for microparticle separation and the cover plate 31 and suctioning the sample liquid using a suction means and/or a suction device, and then inserting a sheath liquid as required between the microchannel chip 1 for microparticle separation and the cover plate 31 and suctioning the sheath liquid. The sample liquid or sheath liquid inserted between the microchannel chip 1 for microparticle separation and the cover plate 31 may be injected between the microchannel chip 1 for microparticle separation and the cover plate 31 using a syringe or the like, or a hole may be provided to the cover plate 31 and the sample liquid and the sheath liquid may be injected from the hole.

The flow rate of the sample liquid and the sheath liquid 32 is preferably 20 to 500 µm/s. When the flow rate is less 20 µm/s, the separation efficiency is reduced due to a reduced ability to wash away blood cells, and when the flow rate is greater than 500 µm/s, any temporarily captured CTCs are suctioned away and separation efficiency is reduced. The flow rate of the sample liquid and the sheath liquid can be adjusted using the suction force of the suction means and/or a suction device.

In the present embodiment, a sheath liquid is allowed flow as required after the sample liquid has first been allowed to flow. Therefore, considerable suction force is required when whole blood or another sample liquid with high viscosity is to be suctioned without aid. Accordingly, when blood is used as the sample liquid, the sample liquid may be diluted 2 to 10 times using a sheath liquid or the like, preferably about 3 to 5 times. In the present embodiment, a meniscus is not generated in sequence in a plurality of main channels 2 by relative movement, but rather, a meniscus can be generated simultaneously in the main channels 2 in the portion where the microchannel chip 1 for microparticle separation and the cover plate 31 overlap, and the time required for separation can therefore be sufficiently reduced even when whole blood has been diluted.

The system for microparticle separation of the present invention may be provided with a magnetic field generator and/or an electric field generator for increasing the efficiency of capturing microparticles in the capture portions. For example, it is possible to install a permanent magnet or an electromagnet as a magnetic field generator on the lower surface of the capture portions to generate a potential field of a magnetic field, and impart magnetism to the CTCs to which magnetic particles marking EpCAM antibodies or the like have been specifically adsorbed, or CTCs to which magnetic particles have been nonspecifically adsorbed (taken in from endocytosis), or other particles desired for capture, and when the system for microparticle separation of the present invention is used, separation from other particles not marked with magnetism can be carried out with good precision.

It is also possible to provide an electrode as an electric field generator on the lower surface of the capture portions or the side surface of the capture portions to generate a potential field of an electric field (in a non-uniform electric field), and to assist capture of CTCs using the polarization of the CTCs and peripheral media and the electrostatic force (Coulomb's force) generated by the slope of the electric field.

The method for detecting captured CTCs may be performed by fluorescent staining using anti-EpCam antibodies or other CTC-specific antibodies marked by FITC or PE, and observation by a fluorescence microscope or the like. When bright-field observation is carried out using an optical microscope, CTCs can be detected using the nucleus, cytoplasm, and other morphological feature in the cell as an indicator with the aid of a Papanicolaou stain or Giemsa stain. In the case of performing long-term observation of the captured CTC, bright-field observation using an optical microscope is preferred.

The present invention is described in detail below using examples, but the examples are used merely for describing the present invention and are provided as reference for concrete modes thereof. Although these examples described specific concrete modes of the present invention, the examples do not limit the scope of the invention disclosed in the present application and do not represent any limitation.

EXAMPLES

Example 1

[Fabrication of a Microchannel Chip for Microparticle Separation]

First, a silicon substrate was organically washed with acetone, ethanol, and ultrapure water, in the stated sequence, using an ultrasonic washer for 5 minutes each at 45 kHz, and then baked for 20 minutes at 145° C. Next, SU-8 was spin-coated onto the silicon substrate and then prebaked for 30 minutes at 95° C. on a hot plate. Exposure was subsequently carried out using a chrome mask in which the shape of the capture portions 3 was substantially octagonal, after which post-exposure baking was carried out for two minutes at 95° C. on a hot plate, and development was performed using a PM thinner. After development, rinsing was carried out using ultrapure water, and the moisture was dispersed and drying was carried out using a spin dryer or the like to end the first processing stage. Next, SU-8 was spin-coated and prebaked for 30 minutes at 95° C. on a hot plate. Exposure was carried out using a chrome mask having the shape of the main channels, after which post-exposure baking was carried out for two minutes at 95° C. on a hot plate, and development was performed using a PM thinner. After development, rinsing was carried out using ultrapure water, and the moisture was dispersed and drying was carried out using a spin dryer or the like to end the second processing stage. The formed pattern was transferred to polydimethylsiloxane (PDMS); and after transfer, the two were separated from each other, and the PDMS surface was hydrophilized using a plasma treatment (frequency 50 kHz and output 700 W for 30 seconds).

Figure 10:
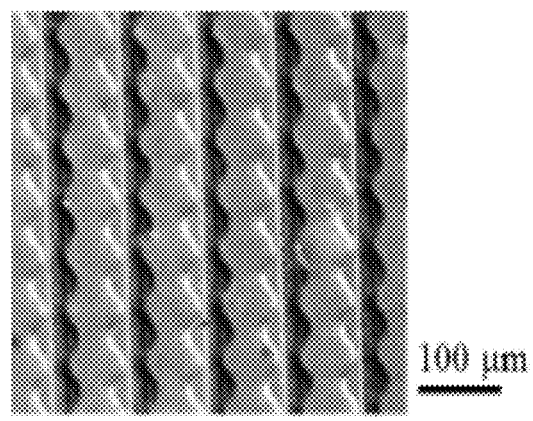
FIG. 10 is a photograph in place of a drawing showing the external appearance of the microchannel chip for microparticle separation obtained in Example 1.

FIG. 10 is a photograph showing the external appearance of the microchannel chip for microparticle separation obtained in Example 1, the size of the microchannel chip for microparticle separation being 30 mm×30 mm. The microchannels have a substantially octagonal shape in which the center of each capture portion matches the center of the channel, the length of the shortest line that passes through the center of the capture portions being about 30 μm and the depth being about 30 μm. The width of the channels is about 10 μm, the depth of the channels in the capture portions is about 20 μm, and the depth of the channels other than in the capture portions is about 50 μm. The center distance between the channels is about 60 μm.

Example 2

In place of the chrome mask of example 1, a chrome mask shown in FIG. 4(1) is used in which a main channel and branching channel are disposed, the branching channel branching from the main channel and reconnecting to the main channel; and a circular capture portion is provided to the branching channel. A microchannel chip for microparticle separation was fabricated using the same procedure as example 1, except that the second stage of processing was not carried out.

Figure 11:
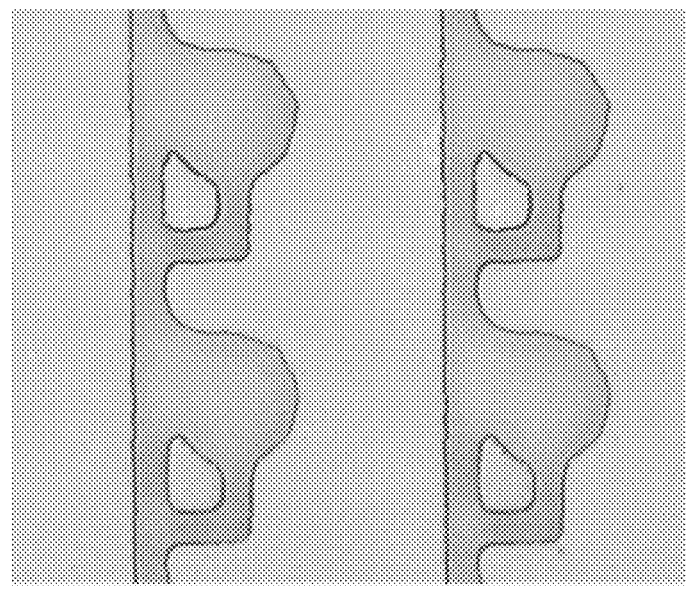
FIG. 11 is a photograph in place of a drawing showing the external appearance of the microchannel chip for microparticle separation obtained in Example 2.

FIG. 11 is a photograph showing the external appearance of the microchannel chip for microparticle separation obtained in Example 2, the size of the microchannel chip for microparticle separation being 30 mm×30 mm. The capture portions are circular in shape having a diameter of about 30 μm. Since formation is carried out in a single stage, the depth in all portions of the main channels and the branching channels is about 30 μm. The width of the main channels and the branching channels is about 8 μm, and the center distance between the main channels is about 80 μm.

Example 3

Other than using a mask having the shape shown in FIG. 4(2) in place of the chrome mask of example 2, a microchannel chip for microparticle separation was fabricated using the same procedure as example 2. The capture portion of the resulting microchannel chip for microparticle separation was substantially square with smooth corners, one side having a length of about 30 μm, and the other dimensions were the same as in example 2.

Example 4

Other than using a mask having the shape shown in FIG. 4(3) in place of the chrome mask of example 2, a microchannel chip for microparticle separation was fabricated using the same procedure as example 2.

Figure 12:
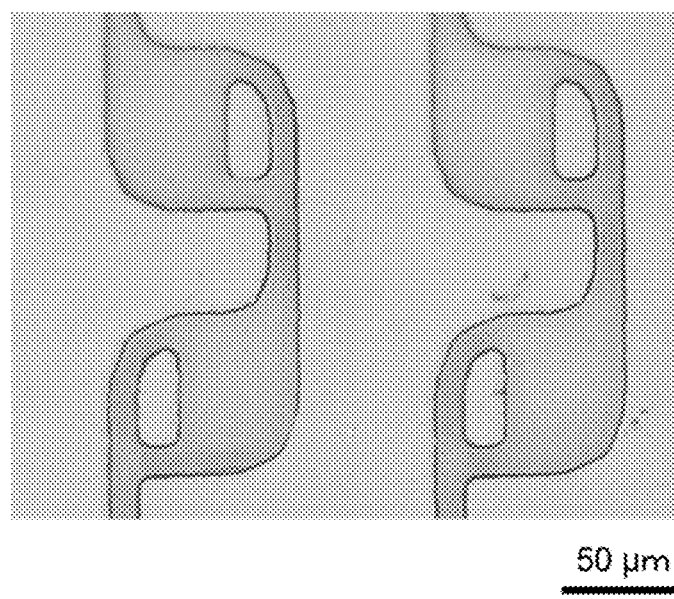
FIG. 12 is a photograph in place of a drawing showing the external appearance of the microchannel chip for microparticle separation obtained in Example 4.

FIG. 12 is a photograph showing the external appearance of the microchannel chip for microparticle separation obtained in Example 4. It is apparent from the photograph that, in contrast to example 2, the position of the main channel in example 4 (and example 3 as well) is different in the upstream side and the downstream side of the capture portions. Therefore, in example 4, the mask is designed so that the position of the main channel matches the position of the main channel in the capture portion one portion to upstream side when a subsequent capture portion is to be provided, but it is also possible to connect the shape shown in FIG. 4(3) and a similar shape so that the main channels are formed in a stepwise fashion. The capture was substantially square with smooth corners, one side having a length of about 30 μm, and the other dimensions were the same as in example 2.

[Fabrication of a Blood Sample]

Cells ($1.0 \times 10^4$) of a stomach cancer cell strain (human stomach cancer-derived cell strain (GCIU-GFP) dispersed by trypsinization) were suspended in 20 μL of drawn human blood to fabricate a blood sample that simulates cancer patient blood. The average particle diameter of the cancer cells was 25 μm.

Example 5

[Fabrication of a System for Microparticle Separation and Experiment for Separating CTCs from a Blood Sample]

A blood sample (20 μL) was injected between the microchannel chips for microparticle separation fabricated in examples 1 to 4 and a 20-mm×20-mm thin glass plate for a sample liquid. The distance between the microchannel chips for microparticle separation and the thin plate for a sample liquid was adjusted to be 700 μm using a microstage. A sheath liquid (10 μL of phosphate-buffered saline (PBS)) was injected between the microchannel chips for microparticle separation and a 10-mm×20-mm thin glass plate for a sheath liquid. The sheath liquid was refilled as needed. The microchannel chips for microparticle separation were moved at a constant speed of 20 μm/s. The flow velocity of the sheath liquid was 20 μm/s.

Figure 13:
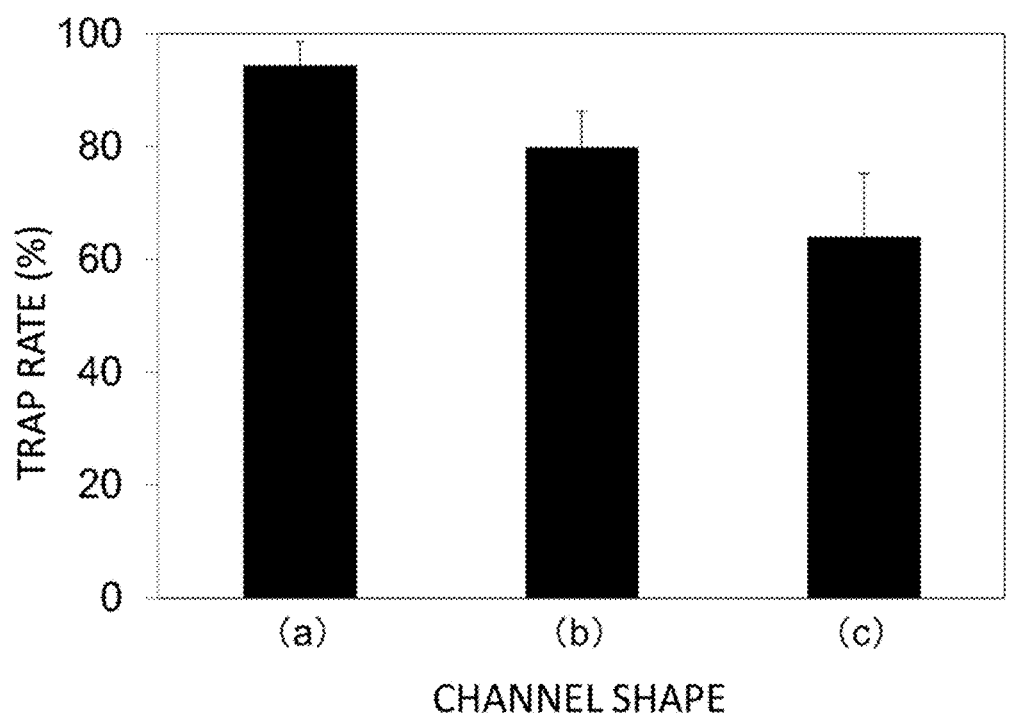
FIG. 13 is a view showing the capture rate when CTCs are separated from a blood sample using the microchannel chip for microparticle separation obtained in examples 1 to 4.

The results of the above-described [Experiment for separating CTCs from a blood sample] are shown in FIG. 13. It is said that only about 1/100 to 1/1000 of CTCs in blood can be captured when CTCs are to be captured using conventional anti-EpCAM antibodies, but it is apparent that the microchannel chip for microparticle separation of the present invention is capable of capturing CTCs with very good efficiency.

In examples 2 to 4 in which a branching channel is provided to the main channel and a capture portion is provided to the branching channel, the CTC capture efficiency was dramatically improved over example 1 in which a capture portion was provided in the main channel. This is ostensibly because when a capture portion is provided in the main channel as in example 1, the captured CTCs deform under fluid force of the sheath liquid and flow out from the capture portions.

On the other hand, in the case of examples 2 to 4, CTCs are captured in capture portions, but it is surmised since the sheath liquid flows through the main channel, the fluid force of the sheath liquid imposed on the CTCs is considerably reduced, the blood cells that flow into the capture portion can pass through the branching channel and again return to the main channel, and CTC capture efficiency is therefore enhanced.

Example 6

A microchannel chip for microparticle separation was fabricated using the same procedure as in example 1 except that the length of the shortest line that passes through the capture portion was about 20 µm, the depth was about 20 µm, and the depth of the channel in the capture portion was about 30 µm.

Example 7

A microchannel chip for microparticle separation was fabricated using the same procedure as in example 2 except that the diameter of the capture portion was about 20 µm and the depth was about 20 µm.

Example 8

A microchannel chip for microparticle separation was fabricated using the same procedure as in example 3 except that length of one side of the capture portion was about 20 µm and the depth was about 20 µm.

Example 9

A microchannel chip for microparticle separation was fabricated using the same procedure as in example 4 except that length of one side of the capture portion was about 20 µm and the depth was about 20 µm.

[Fabrication of a Polystyrene-Bead Suspension]

A sample liquid in which 18-µm polystyrene beads and 7-µm polystyrene beads were suspended in 20 µL of pure water was fabricated.

Example 10

[Experiment for Separating Out 18-µm Polystyrene Beads from a Polystyrene-Bead Suspension]

The separation experiment was carried out using the same procedure as described above in the "experiment for separating CTCs from a blood sample," except that the microchannel chip for microparticle separation fabricated in example 6 to 9 was used and ultrapure water was used as the sheath liquid. When beads that do not readily change shape were separated out, it was confirmed a majority of the 18-µm polystyrene beads were trapped using chips having the shapes in any of examples 6 to 9.

Example 11

[Fabrication of the System for Microparticle Separation]

A mold for a suction unit was fabricated, and the shape of the mold was transferred to PDMS to fabricate the suction unit. The suction unit was 6 mm in width and 30 mm in length, the lateral groove was 160 µm in width, and the suction hole was 1 mm in diameter. One end of a silicone tube (manufactured by As One Corporation) was connected to the suction hole, and the other end was connected to a micro-syringe (manufactured by KD Scientific). A cover plate made of glass was fabricated to 22 mm×30 mm. The resulting structure was combined with the microchannel chip for microparticle separation fabricated in Example 2 to fabricate a system for microparticle separation.

Example 12

[Blood Sample Preparation]

A blood sample fabricated using the procedure described in "Fabrication of a blood sample" above was diluted five times using a sheath liquid to fabricate a sample liquid.

[Experiment for Suctioning a Blood Sample Liquid]

A suction unit was arranged on the drain channel of the microchannel chip for microparticle separation fabricated in Example 11. The gap between the microchannel chip for microparticle separation and the cover plate was set to 2 mm on the suction unit side and 2 mm on the opposite side from the suction unit. Next, 750 µL of a fabricated sample liquid was injected between the microchannel chip for microparticle separation and the cover plate, and the micro-syringe was adjusted so that the speed of the sample liquid flowing through the main channels was 400 µm/s.

Figure 14:
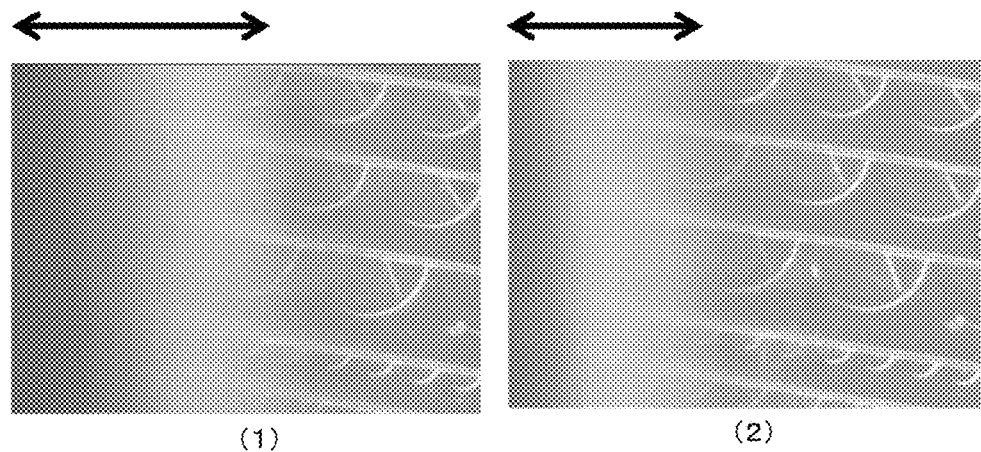
FIG. 14 is a photograph in place of a drawing showing that suctioning a sample liquid offsets the position in which the meniscus is generated in Example 12.

FIG. 14 is a photograph showing that a suctioning sample liquid offsets the position in which the meniscus is generated in Example 12, and FIG. 14(2) is a photograph after 15 seconds have elapsed from FIG. 14(1). It is apparent from a comparison of the photographs in FIGS. 14(1) and (2) that suctioning the sample liquid has moved the line of the generated meniscus. The sample liquid was observed by fluorescence microscope after the sample liquid was suctioned, and was confirmed that CTCs had been captured in the capture portions.

Example 13

[Fabrication of a Polystyrene-Bead Suspension]

A sample liquid was fabricated in which 20-µm polystyrene beads and 3-µm beads were suspended in concentrations of $2.4\times10^6$/mL and $1.1\times10^4$/mL, respectively, in pure water.

[Experiment for Separating Out 20-µm Polystyrene Beads from a Polystyrene-Bead Suspension]

Figure 15:
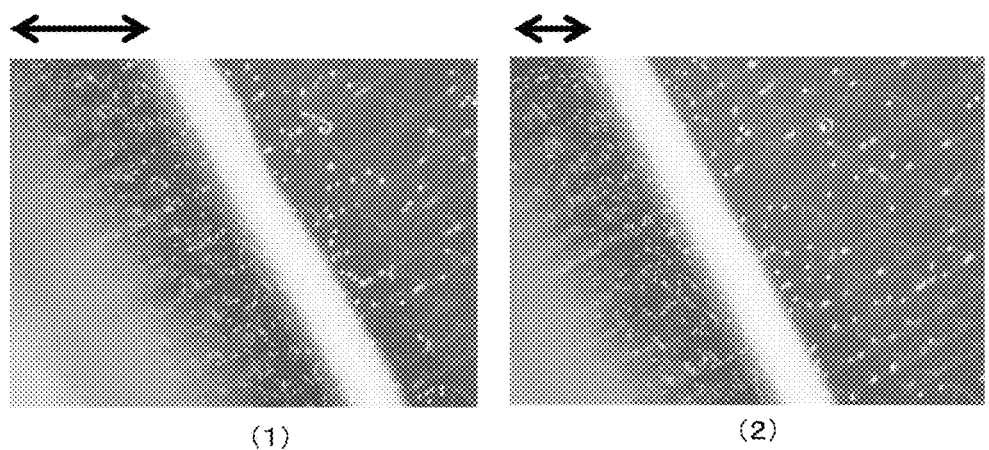
FIG. 15 is a photograph in place of a drawing showing that suctioning a sample liquid offsets the position in which the meniscus is generated and that beads having a diameter of 20 μm are captured in capture portions in Example 13.

The separation experiment was carried out using the same procedure as described above Example 12, except that a polystyrene-bead suspension was used as the sample liquid in place of the blood sample liquid. FIG. 15 is a photograph showing that suctioning a sample liquid offsets the position in which the meniscus is generated and that beads having a diameter of 20 µm are captured in capture portions in Example 13, and FIG. 15(2) is a photograph after 7 seconds have elapsed from FIG. 15(1). It is apparent from a comparison of the photographs in FIGS. 15(1) and (2) that suctioning the sample liquid has moved the line of the generated meniscus. Also, it was confirmed that 20-μm polystyrene beads had been captured in the capture portions after the meniscus line had passed.

From the results of the foregoing, the system for microparticle separation of the present invention was confirmed to be capable of separating out wide particles with good efficiency without regard for microparticles that readily change shape or microparticles that are not likely to change shape, by varying the shape of the capture portions and the channels of the microchannel chip for microparticle separation.

INDUSTRIAL APPLICABILITY

Using the system for microparticle separation comprising the microchannel chip for microparticle separation of the present invention makes it possible to rapidly separate out microparticles of different sizes in a sample with high efficiency without the use of antibodies or the like. Separation of CTCs from whole blood and other applications are therefore very effective in a clinical setting, and the system can therefore be used as a system for cancer diagnosis in hospitals, emergency centers, and other medical institutions, as well as in university medical departments and other research institutions and educational institutions.

The invention claimed is:

1. A microchannel chip for microparticle separation, the microchannel chip having an upper surface and a bottom surface, the microchannel chip comprising:
   a plurality of main channels formed at the upper surface and extending along the upper surface, wherein:
   each of the plurality of main channels includes a plurality of capture portions and remaining portions other than the plurality of capture portions,
   each of the plurality of capture portions has a greater width than a width of the remaining portions of the plurality of main channels in a top view,
   in a cross section, each of the plurality of capture portions has an upper portion and a bottom portion disposed below the upper portion,
   the upper portion has a greater width than the bottom portion, and
   a depth of the upper portion is smaller than a depth of the remaining portions.

2. The microchannel chip for microparticle separation according to claim 1, further comprising a drainage channel connected to one end of each of the plurality of main channels.

3. A system for microparticle separation, the system comprising:
   the microchannel chip for microparticle separation according to claim 1;
   a first plate for sample liquid disposed above at least part of the plurality of main channels and being relatively movable with respect to the microchannel chip to generate a meniscus;
   a second plate for sheath liquid disposed above at least part of the plurality of main channels and being movable with respect to the microchannel chip to generate a meniscus; and
   at least one of a suction material and a suction device for suctioning sheath liquid.

4. A system for microparticle separation, the system comprising:
   the microchannel chip for microparticle separation according to claim 1;
   a cover plate disposed above at least part of the plurality of main channels, to generate a meniscus; and
   at least one of a suction material and a suction device.

5. The system for microparticle separation according to claim 3, further comprising a suction unit having a base, a lateral groove which is formed in the base and a suction hole in communication with the lateral groove.

6. The system for microparticle separation according to claim 4, further comprising a suction unit having a base, the lateral groove which is formed in the base and the suction hole in communication with the lateral groove.

7. The system for microparticle separation according to claim 3, wherein at least one of a magnetic field generator and an electric field generator is provided in the plurality of capture portions of the microchannel chip for microparticle separation.

8. The microchannel chip for microparticle separation according to claim 1, wherein a width A of each of the bottom portion of each of the plurality of capture portions satisfies Y<A<X, where X is from 15 μm to 1mm, and Y is 7 μm.

9. A microchannel chip for microparticle separation, the microchannel chip comprising:
   a substrate having an upper surface and a bottom surface; and
   a plurality of channels formed at the upper surface of the substrate and extending along the upper surface, wherein:
   an entirely of each of the plurality of channels is a groove with an upper portion thereof being opened,
   each of the plurality of channels includes a main portion having a first depth and a first width and a plurality of capture portions, and
   each of the plurality of capture portions has:
      a shallow portion having a second depth smaller than the first depth of the main portion and a second width greater than the first width, and
      a deep portion disposed below the shallow portion and having a third depth and the first width.

10. The microchannel chip for microparticle separation according to claim 9, wherein a sum of the second depth and the third depth is equal to the first depth.

11. The microchannel chip for microparticle separation according to claim 10, wherein the first width is between 8 to 12 μm.

12. The microchannel chip for microparticle separation according to claim 10, wherein the second width is between 16 to 36 μm.

13. The microchannel chip for microparticle separation according to claim 10, wherein the second depth is between 16 to 36 μm and the third depth is between 8 to 20 μm.

14. The microchannel chip for microparticle separation according to claim 9, wherein ends of the plurality of channels are connected to a drainage channel.

15. The microchannel chip for microparticle separation according to claim 9, wherein the substrate is made of one of polydimethylsiloxane, poly(methyl methacrylate), polycarbonate, polyethylene, hydrogel and glass.

16. The microchannel chip for microparticle separation according to claim 15, wherein the surface of the substrate is hydrophilic.

17. The microchannel chip for microparticle separation according to claim 3, wherein:
   the suction material is one of fabric, cotton, sponge and chamois, and
   the suction device is a pump.

18. The microchannel chip for microparticle separation according to claim 4, wherein:
the suction material includes at least one of fabric, cotton, sponge and chamois, and
the suction device is a pump.

19. The microchannel chip for microparticle separation according to claim 8, wherein a width B of the upper portion of each of the plurality of capture portions satisfies 1X<B<10X.

20. The microchannel chip for microparticle separation according to claim 8, wherein a depth C of the upper portion of each of the plurality of capture portions satisfies 1X<C<10X, a depth D of the bottom portion of each of the plurality of capture portions satisfies Y<D, and a depth E of the remaining portions of the plurality of main channels other than the plurality of capture portions satisfies E=C+D.

21. The microchannel chip for microparticle separation according to claim 19, wherein the width B satisfies 1X<B<2X.

22. The microchannel chip for microparticle separation according to claim 20, wherein the width C satisfies 1X<C<2X.

23. The microchannel chip for microparticle separation according to claim 8, wherein the width A satisfies Y<A<0.8X.

24. The microchannel chip for microparticle separation according to claim 3, wherein:
the suction material is one of fabric, cotton, sponge and chamois, and
the suction device is a micro-syringe.

25. The microchannel chip for microparticle separation according to claim 4, wherein:
the suction material includes at least one of fabric, cotton, sponge and chamois, and
the suction device is a micro-syringe.

* * * * *